(12) United States Patent
Schmoyer

(10) Patent No.: US 6,419,936 B1
(45) Date of Patent: Jul. 16, 2002

(54) TOPICAL SKIN OINTMENT

(76) Inventor: Adell J. Schmoyer, 2120 Barcelona Way, S., St. Petersburg, FL (US) 33712

( * ) Notice: Subject to any disclaimer, the term of this patent is extended or adjusted under 35 U.S.C. 154(b) by 0 days.

(21) Appl. No.: 09/599,060

(22) Filed: Jun. 21, 2000

(51) Int. Cl.[7] .................................................. A61K 7/00
(52) U.S. Cl. ........................ 424/401; 424/614; 424/450; 424/78.05; 424/78.06
(58) Field of Search ................. 424/401, 614, 424/78.05, 59, 450, 78.06

(56) References Cited

U.S. PATENT DOCUMENTS

| | | | |
|---|---|---|---|
| 5,362,488 A | * | 11/1994 | Sibley ..................... 424/78.05 |
| 5,597,575 A | * | 1/1997 | Breitbarth .................... 424/401 |
| 6,071,541 A | * | 1/1999 | Murad ........................ 424/616 |
| 5,993,787 A | * | 11/1999 | Sun et al. ..................... 424/59 |

* cited by examiner

Primary Examiner—Jose' G. Dees
Assistant Examiner—Mina Haghighatian
(74) Attorney, Agent, or Firm—Joseph N. Breaux

(57) ABSTRACT

A topical skin ointment for application onto the skin of individuals suffering from minor skin irritations such as dry chapped skin, minor cuts, and scrapes and abrasions. The topical skin ointment includes ingredients to reduce the discomfort associated with these types of skin irritations as well ingredients to promote the natural healing process.

1 Claim, 1 Drawing Sheet

TOPICAL SKIN OINTMENT

TECHNICAL FIELD

The present invention relates to skin creams and more particularly to a topical skin ointment that provides reliefe from skin irritations; the topical skin ointment including the following ingredients: Vitamin E in an oil base, Vitamin A and D ointments, Zinc Oxide ointment, Aloe Vera extract; the ingredients being combined in the following quantities twenty thousand units of Vitamin E in the oil base, two ounces of Vitamin A and D ointment, one ounce of Zinc Oxide ointment and one ounce Aloe Vera extract.

BACKGROUND ART

Individuals often suffer from minor skin irritations such as dry chapped skin, minor cuts, and scrapes and abrasions. It would be a benefit to these individuals to have an ointment that could be applied that would reduce the discomfort associated with these types of skin irritations as well as promote the natural healing process.

GENERAL SUMMARY DISCUSSION OF INVENTION

It is thus an object of the invention to provide a topical skin ointment that includes including the following ingredients: Vitamin E in an oil base, Vitamin A and D ointments, Zinc Oxide ointment, Aloe Vera extract; the ingredients being combined in the following quantities twenty thousand units of Vitamin E in the oil base, two ounces of Vitamin A and D ointment, one ounce of Zinc Oxide ointment and one ounce Aloe Vera extract.

Accordingly, a topical skin ointment is provided. The topical skin ointment includes including the following ingredients: Vitamin E in an oil base, Vitamin A and D ointments, Zinc Oxide ointment, Aloe Vera extract; the ingredients being combined in the following quantities twenty thousand nits of Vitamin E in the oil base, two ounces of Vitamin A and D ointment, one ounce of Zinc Oxide ointment, and one ounce Aloe Vera extract. In preferred embodiments of the topical skin ointment one-half ounce of one-percent Clortrimazole ointment and/or one ounce of Desitin™ ointment may also be included.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
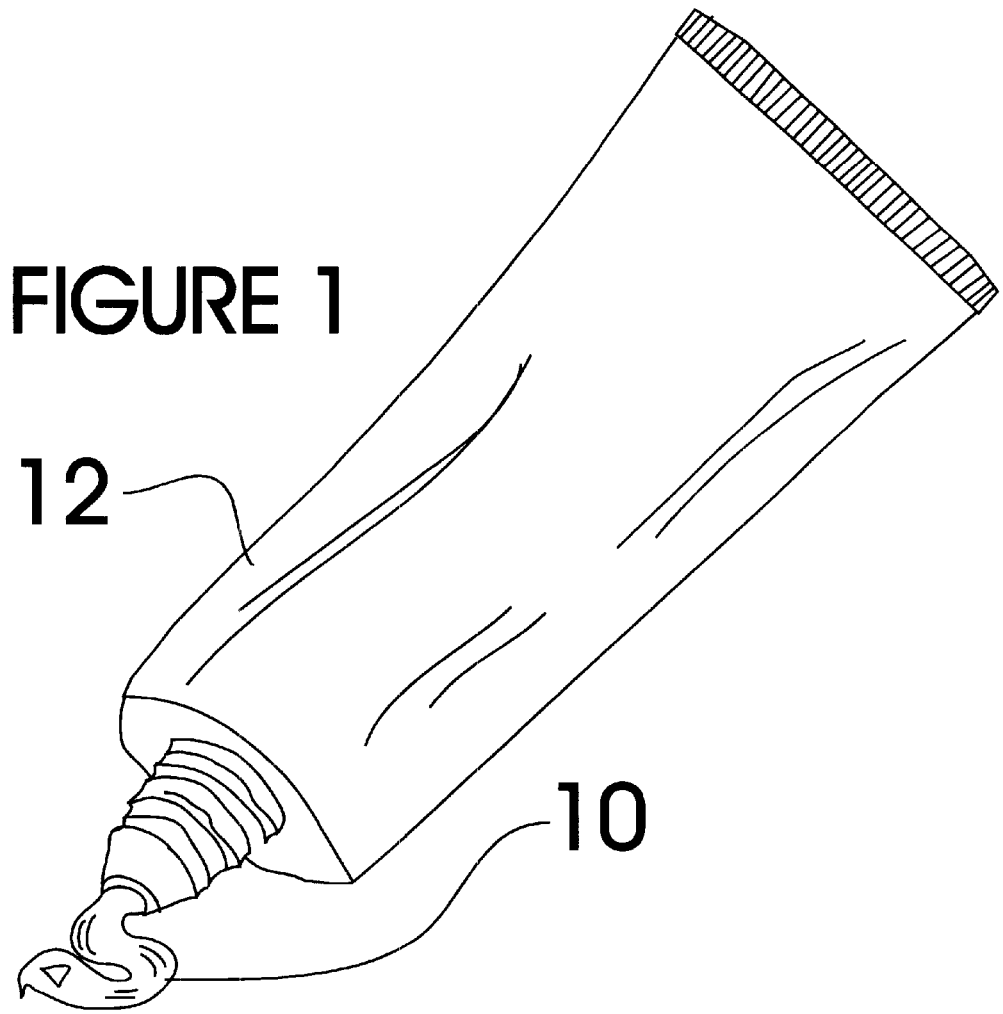
FIG. 1 is a perspective view of a tube filled with the topical skin ointment of the present invention.

FIG. 1 shows an exemplary topical skin ointment 10 of the present invention packaged in a conventional squeeze tube 12 is provided. The topical skin ointment 10 includes including the following ingredients: Vitamin E in an oil base, Vitamin A and D ointments, Zinc Oxide ointment, Aloe Vera extract, Clortrimazole ointment and Desitin™ ointment; the ingredients being combined in the following quantities twenty thousand units of Vitamin E in the oil base, two ounces of Vitamin A and D ointment, one ounce of Zinc Oxide ointment, one-half ounce of one-percent Clortrimazole ointment, one ounce of Desitin™ ointment and one ounce Aloe Vera extract.

It can be seen from the preceding description that a topical skin ointment has been provided.

It is noted that the embodiment of the topical skin ointment described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A topical skin ointment comprising:

Vitamin E in an oil base;

Vitamin A ointment;

Vitamin D ointment;

Zinc Oxide ointment; and

Aloe Vera extract;

the ingredients being combined in the following quantities twenty thousand units of Vitamin E in the oil base, two ounces of Vitamin A ointment and Vitamin D ointment, one ounce of Zinc Oxide ointment, and one ounce Aloe Vera extract.

* * * * *